US011141528B1

(12) United States Patent
Schmitz et al.

(10) Patent No.: US 11,141,528 B1
(45) Date of Patent: Oct. 12, 2021

(54) THERAPEUTIC FLUID DELIVERY CARTRIDGE

(71) Applicants: Thomas Leroy Schmitz, Woodbury, MN (US); Jesse James Corry, Woodbury, MN (US)

(72) Inventors: Thomas Leroy Schmitz, Woodbury, MN (US); Jesse James Corry, Woodbury, MN (US)

( * ) Notice: Subject to any disclaimer, the term of this patent is extended or adjusted under 35 U.S.C. 154(b) by 0 days.

(21) Appl. No.: 17/121,715

(22) Filed: Dec. 14, 2020

(51) Int. Cl.
*A61M 5/158* (2006.01)
*A61M 5/165* (2006.01)
*A61M 5/168* (2006.01)
*A61M 5/142* (2006.01)

(52) U.S. Cl.
CPC .... *A61M 5/16804* (2013.01); *A61M 5/14244* (2013.01); *A61M 5/158* (2013.01); *A61M 5/165* (2013.01); *A61M 5/16881* (2013.01); *A61M 2005/14208* (2013.01); *A61M 2005/1652* (2013.01); *A61M 2202/0007* (2013.01); *A61M 2202/0415* (2013.01); *A61M 2202/0437* (2013.01); *A61M 2205/3306* (2013.01); *A61M 2205/3334* (2013.01); *A61M 2205/3553* (2013.01); *A61M 2205/502* (2013.01); *A61M 2205/8206* (2013.01)

(58) Field of Classification Search
CPC .......... A61M 5/16804; A61M 5/14244; A61M 5/158; A61M 5/165; A61M 5/16881; A61M 5/145; A61M 5/1408; A61M 5/16877; A61M 2005/14268; A61M 2005/14208; A61M 2005/1652; A61M 1/16; A61M 1/0058; A61J 2205/10–60; A61F 2/46; A61B 17/1675; A61B 17/56; A61B 2017/564; A61L 2430/00; A61L 2430/24
See application file for complete search history.

(56) References Cited

U.S. PATENT DOCUMENTS

| 5,164,597 | A | 11/1992 | Lodder |
| 5,378,233 | A | 1/1995 | Haber et al. |
| 5,382,229 | A | 1/1995 | Grabenkort et al. |
| 5,628,731 | A * | 5/1997 | Dodge ................ A61M 1/0058 604/153 |
| 6,024,720 | A | 2/2000 | Chandler et al. |

(Continued)

OTHER PUBLICATIONS

Ateschrang et al., Septic arthritis of the knee: Presentation of a novel irrigation-suction system tested in a cadaver study, BMC Musculoskeletal Disorders, Aug. 7, 2011, Germany.

(Continued)

*Primary Examiner* — Nathan R Price
*Assistant Examiner* — Justin L Zamory
(74) *Attorney, Agent, or Firm* — Lund IP, PLLC

(57) ABSTRACT

An external medical device includes a first cartridge bay with a first cartridge port, a second cartridge bay with a second cartridge port, a fluid outlet in fluid communication with the first cartridge port, a fluid pump configured to deliver a therapeutic fluid from a fluid cartridge engaged with the first cartridge port through the fluid outlet in response to fluid outlet control signals, a fluid inlet in fluid communication with the second cartridge port, and a fluid control structure in fluid communication with the fluid inlet to control fluid flow through the fluid inlet.

20 Claims, 8 Drawing Sheets

(56) References Cited

U.S. PATENT DOCUMENTS

| | | | | |
|---|---|---|---|---|
| 6,325,788 | B1* | 12/2001 | McKay | A61M 1/0005 |
| | | | | 604/120 |
| 7,771,716 | B2 | 8/2010 | Hedrick et al. | |
| 8,591,486 | B2 | 11/2013 | Locke et al. | |
| 10,864,321 | B1 | 12/2020 | Schmitz et al. | |
| 2004/0256329 | A1 | 12/2004 | Meserol et al. | |
| 2006/0051396 | A1 | 3/2006 | Hamilton et al. | |
| 2009/0266358 | A1* | 10/2009 | Sacristan Rock | A61M 16/18 |
| | | | | 128/203.26 |
| 2012/0016306 | A1* | 1/2012 | Lee | A61M 5/152 |
| | | | | 604/153 |
| 2015/0025311 | A1 | 1/2015 | Kadan et al. | |
| 2018/0236212 | A1* | 8/2018 | Chida | A61M 25/065 |
| 2019/0275243 | A1* | 9/2019 | Deck | A61M 5/1408 |
| 2020/0046888 | A1 | 2/2020 | Locke et al. | |
| 2020/0246194 | A1* | 8/2020 | Gonzalez | A61M 1/0092 |

OTHER PUBLICATIONS

Hamblin, Can osteoarthritis be treated with light?, Arthritis Research & Therapy, Oct. 29, 2013, Germany.

Khoo et al., Bedside Continuous Irrigation and Drainage as an Interim Local Treatment for Septic Arthritis of the Knee in the Medically Unstable Patient: A Case Report, Malaysian Orthopaedic Journal, Jun. 2015, Malaysia.

* cited by examiner

THERAPEUTIC FLUID DELIVERY CARTRIDGE

TECHNICAL FIELD

This disclosure relates to external medical devices.

BACKGROUND

Synovial joints include connective tissue structures that enclose a joint capsule the joint. A fibrous layer seals the bones of the joint and joint capsule is filled with synovial fluid. Most joints of a mammal are synovial joints, including hinge joints, such as elbow, knee, ankle, and interphalangeal joints, ball-and-socket joints, such as hip and shoulder joints, condyloid joints, such as metacarpophalangeal joints of the fingers and radiocarpal joint of the wrist, facet joints, such as vertebral joints, and others.

Injuries to tissues within joint capsules are generally slow to heal. For example, the lack of blood flow within a joint capsule limits natural healing supported by blood flow, such the delivery of oxygen and nutrients. For this reason, damaged and degraded tissues within a joint capsule are often represent chronic injuries. Such injuries include partially and completely torn ligaments, torn or worn meniscus, worn cartilage, and arthritis.

Such injuries may require surgical intervention and/or lifetime management, such as physical therapy and pain management techniques. However, even in the case of surgical intervention to tissues within a joint capsule, healing times are often measured in months or even years, significantly longer recovery periods than are common with soft tissue injuries in which blood flow supports natural healing.

BRIEF SUMMARY

This disclosure is directed to techniques for delivering therapeutic fluid from a cartridge to a joint capsule of a patient. The disclosed techniques include a portable joint capsule fluid delivery device, which facilitates short term and long term treatment of a joint capsule with a therapeutic fluid. Also disclosed are techniques for delivery of therapeutic fluids to joint capsules to aid in rejuvenation and healing. In various examples, such therapeutic fluids may include stem cells, blood or components thereof, such as platelet-rich plasma, micro-fragmented adipose tissue, Wharton's jelly, saline or other irrigation fluid, antiseptic fluids and others. In some examples, treatment may include circulating therapeutic fluid through the joint capsule and recapturing circulated fluid with the portable joint capsule fluid delivery device.

In one example, this disclosure is directed to an external medical device including a first cartridge bay with a first cartridge port, a second cartridge bay with a second cartridge port, a fluid outlet in fluid communication with the first cartridge port, a fluid pump configured to deliver a therapeutic fluid from a fluid cartridge engaged with the first cartridge port through the fluid outlet in response to fluid outlet control signals, a fluid inlet in fluid communication with the second cartridge port, and a fluid control structure in fluid communication with the fluid inlet to control fluid flow through the fluid inlet.

In another example, this disclosure is direct to a method for delivering fluid to a joint capsule of a patient. The method includes storing an identification of a first cartridge in a memory of a control module, sending instructions based on the stored identification, from the control module to a fluid pump of an external medical device, to activate the pump in order to deliver the therapeutic fluid from the first cartridge via a fluid outlet of the external medical device into the joint capsule via a first tubing segment, and sending instructions based on the stored identification, from the control module to a fluid control structure of the external medical device, to operate the fluid control structure in order to control flow from the joint capsule via a second tubing segment into a second cartridge via a fluid inlet of the external medical device.

DETAILED DESCRIPTION

FIGS. 1A-3 illustrate a portable joint capsule fluid delivery device 100. Device 100 is configured to deliver a therapeutic fluid from a therapeutic fluid cartridge to a joint capsule of the patient. Device 100 accepts therapeutic fluid cartridges, which may include any of a variety of therapeutic fluids. Device 100 includes hinged doors 106A, 106B (collectively, "doors 106") within housing 101 for accessing cartridge bays 170A, 170B (collectively, "bays 170"). Bay 170A includes port 172A for receiving a therapeutic fluid cartridge. Meanwhile, bay 170B includes port 172B for receiving an empty cartridge to facilitate flushing a joint capsule with therapeutic fluid. Ports 172A, 172B are collectively referred to as "ports 172."

Figure 2A:
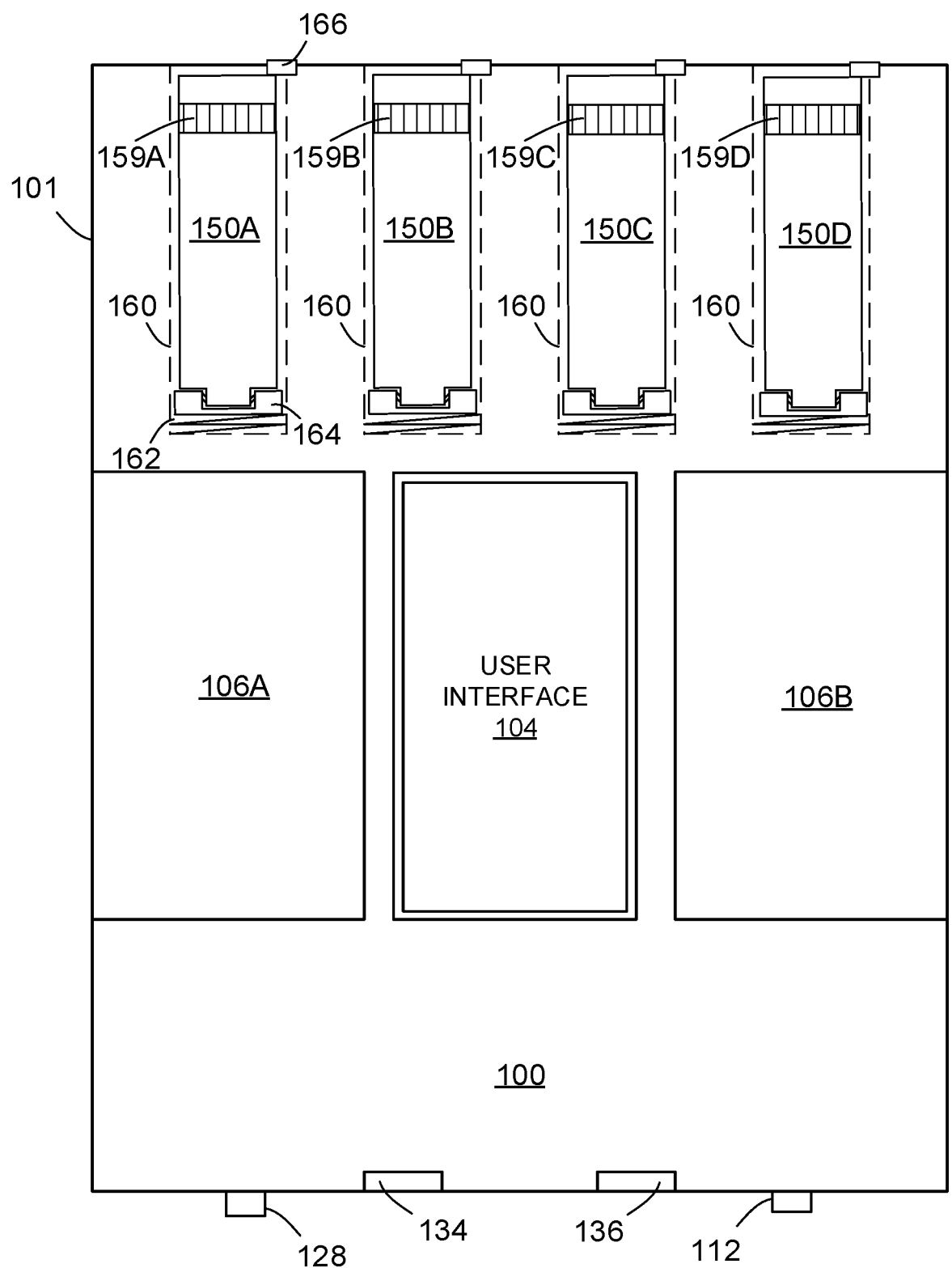
FIGS. 2A-2D are conceptual diagrams of a portable joint capsule fluid delivery device.

As shown in FIG. 2A, housing 101 includes optional recessed cartridge storage receptacles 160 for storing therapeutic fluid cartridges 150A-150D (collectively, "cartridges 150") prior or after use. Volumes of cartridges 150 may vary, but are suitable for mobility of device 100, Example volumes may be in the range of about 30 to 350 milliliters and/or about 1 to 12 fluid ounces.

Figure 1A:
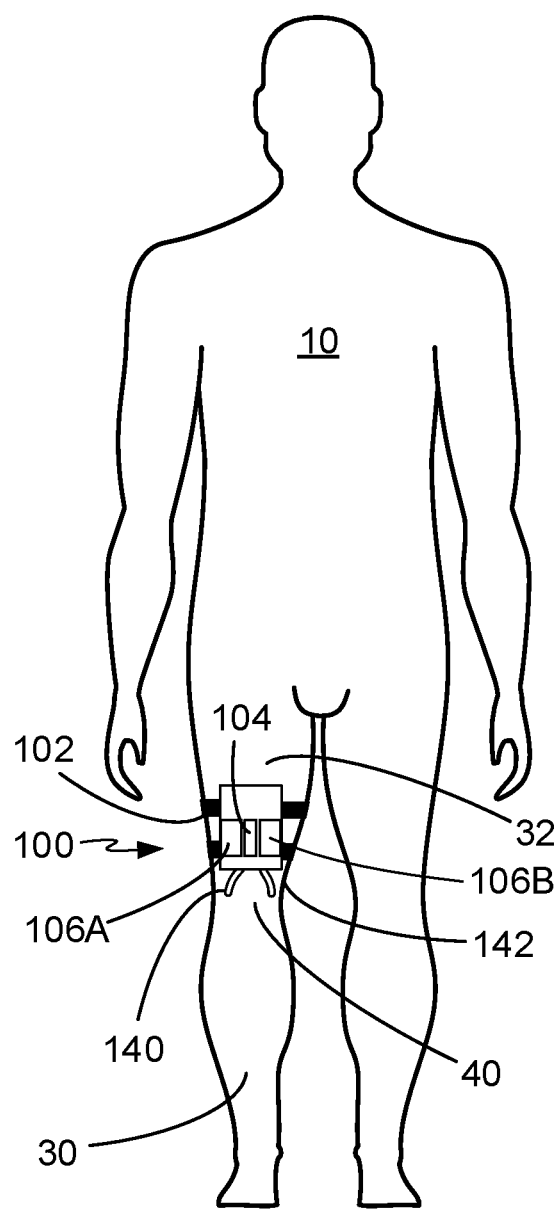
FIG. 1A is a conceptual diagram of a human patient receiving treatment to their right knee with a portable joint capsule fluid delivery device.
Figure 1B:
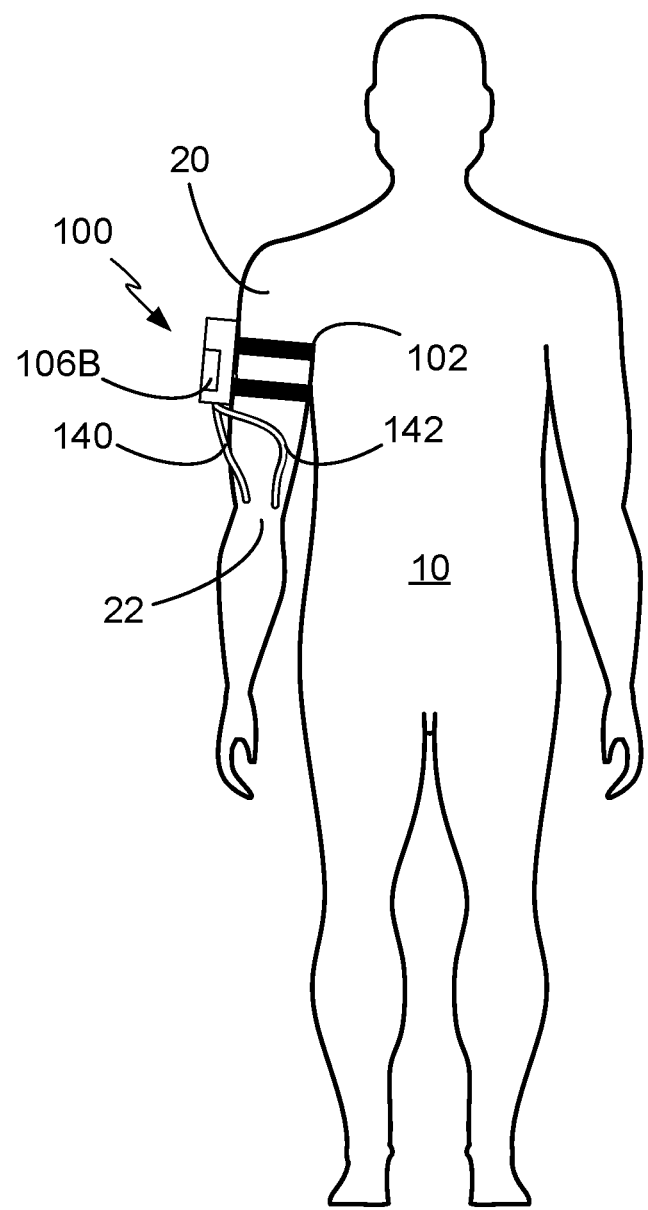
FIG. 1B is a conceptual diagram of a human patient receiving treatment to their left elbow with a portable joint capsule fluid delivery device.
Figure 2B:
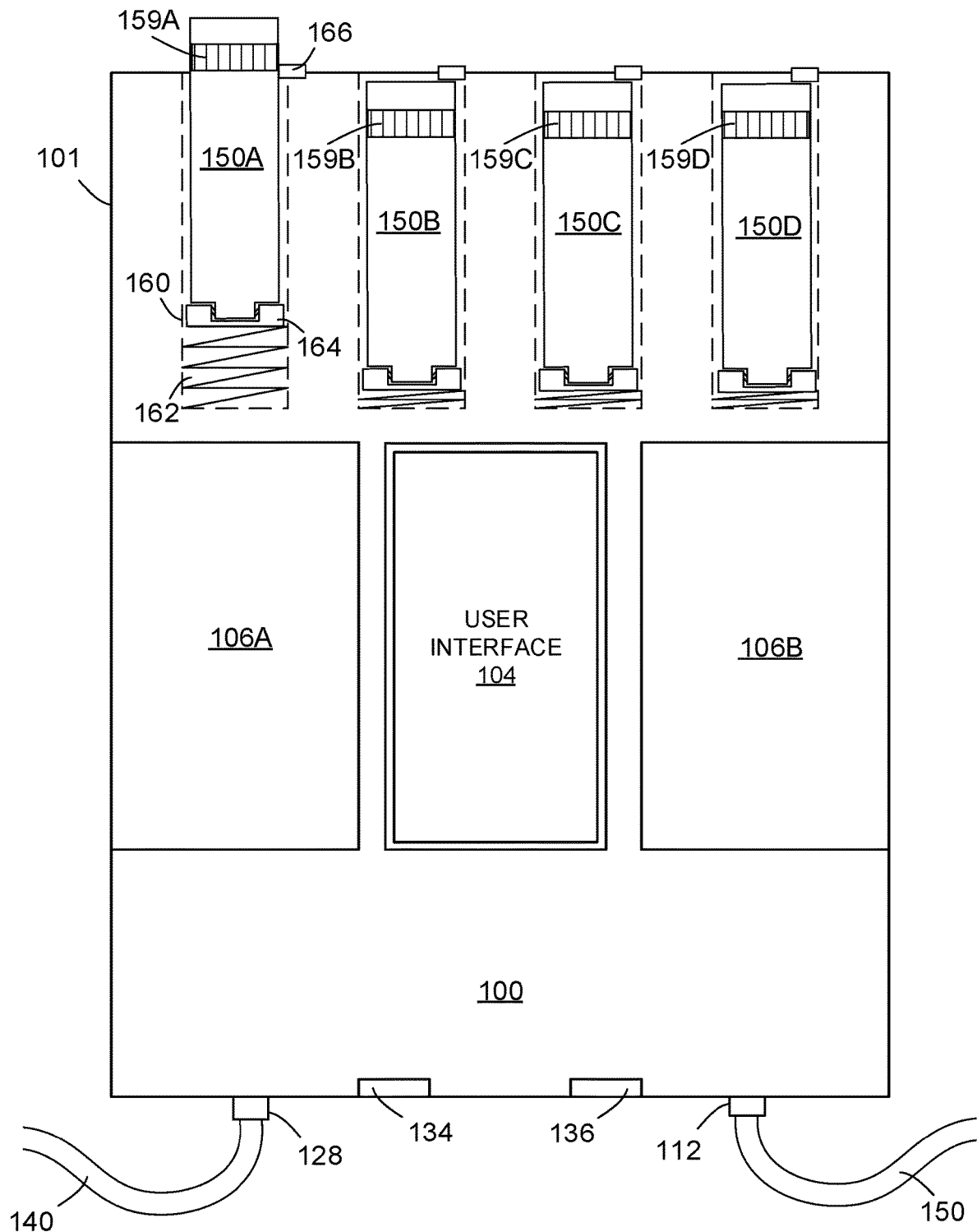
Figure 2C:
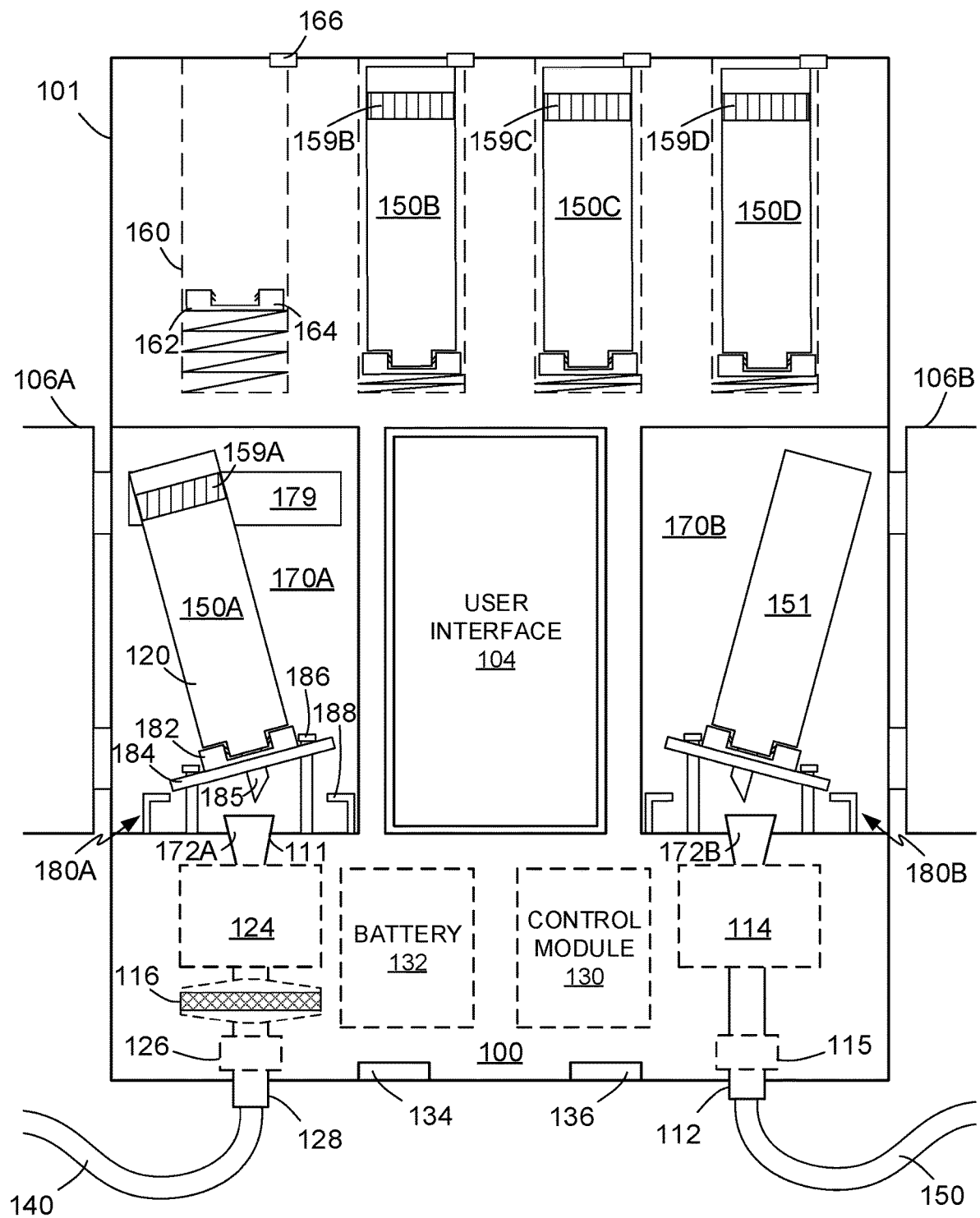
Figure 2D:
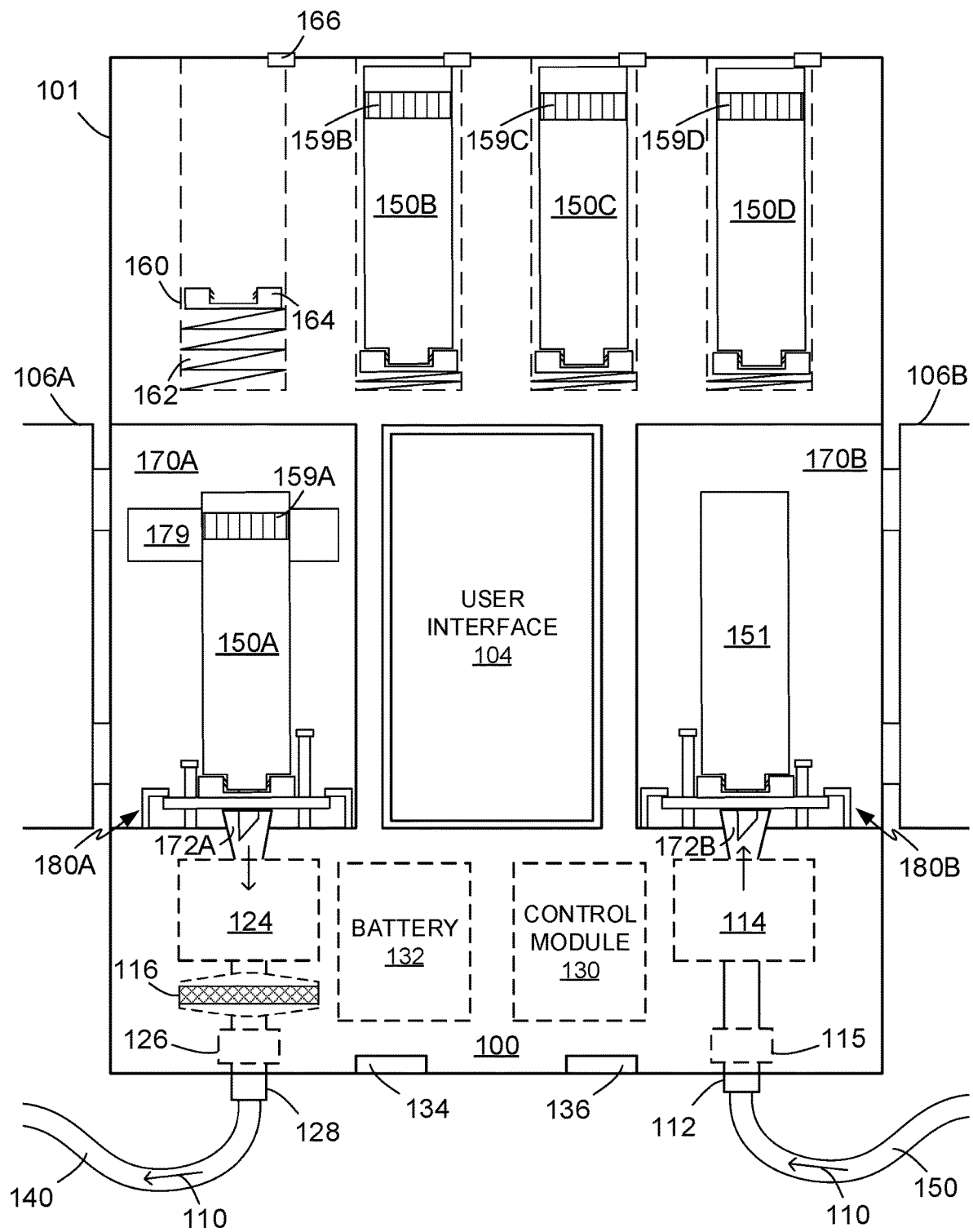
Figure 3:
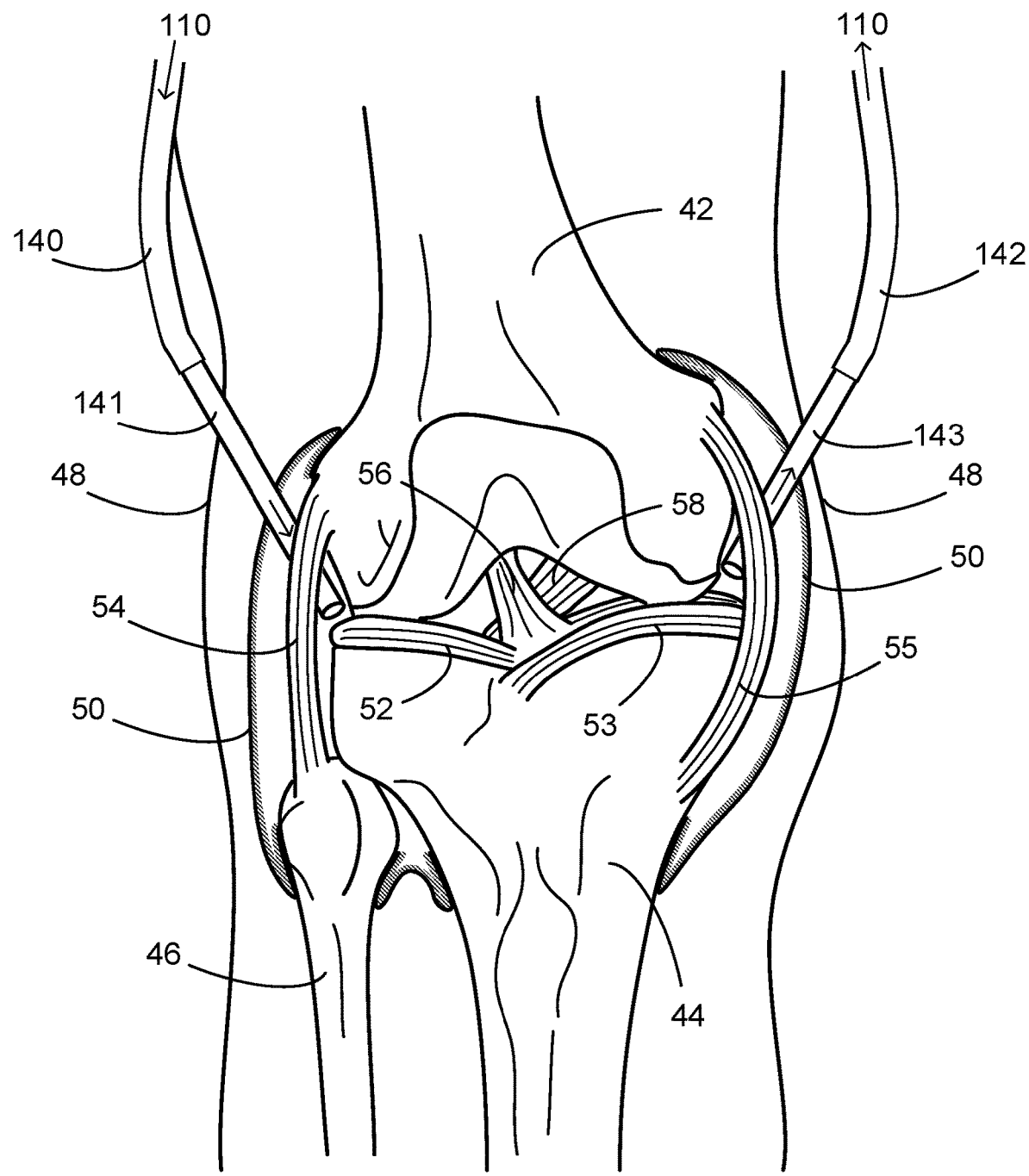
FIG. 3 is an anatomical illustration of a knee of a patient receiving treatment with a portable joint capsule fluid delivery device.

FIG. 1A is a conceptual diagram of a human patient 10 receiving treatment to their right knee 40 with portable joint capsule fluid delivery device 100, whereas FIG. 1B is a conceptual diagram of human patient 10 receiving treatment to their left elbow 22 with device 100. FIG. 2A illustrates device 100 with therapeutic fluid cartridges 150 stored in recessed cartridge storage receptacles 160, and FIG. 2B illustrates therapeutic fluid cartridge 150A partially removed from its receptacle 160. FIG. 2C illustrates therapeutic fluid cartridge 150A within cartridge bay 170A and an empty cartridge 151 within cartridge bay 170B, and FIG. 2D illustrates therapeutic fluid cartridge 150A fluidly connected to port 172A within cartridge bay 170A and empty cartridge 151 fluidly connected to port 172B within cartridge bay 170B. FIG. 3 is an anatomical illustration of right knee 40 of patient 10 receiving treatment with portable joint capsule fluid delivery device 100.

Device 100 is configured to deliver a therapeutic fluid from a therapeutic fluid cartridge 150 to a joint capsule of a patient, and to receive a return flow of fluid from the joint capsule, filling an empty cartridge 151. Portable joint capsule fluid delivery device 100 includes a therapeutic fluid cartridge bay 170A with a therapeutic fluid cartridge port 172A. Portable joint capsule fluid delivery device 100 further includes a cartridge bay 170B with a cartridge port 172B. To facilitate delivery of a therapeutic fluid, a therapeutic fluid cartridge 150 is fluidly connected to cartridge port 172A. To facilitate flushing a joint capsule with a therapeutic fluid, an empty cartridge 151 fluidly connected to port 172B within cartridge bay 170B. Device 100 includes a housing 101 forming cartridge bays 170A, 170B, as well as recessed cartridge storage receptacles 160.

To initiate delivery of a therapeutic fluid, a user first removes a therapeutic fluid cartridge 150 from the associated recessed cartridge storage receptacle 160. Each cartridge storage receptacle 160 includes a spring 162 with mounting features 164 engaged a mouth of a cartridge. In various example, mounting features 164 may include a press fit, screw threads, gasket and/or other connection features. Recessed cartridge storage receptacle 160 includes tab 166 to maintain spring 162 in a compressed state while storing a therapeutic fluid cartridge. To remove the therapeutic fluid cartridge stored in the cartridge storage receptacle 160, the user pulls tab 166, allowing spring 162 to push the therapeutic fluid cartridge 150A from the cartridge storage receptacle 160 (FIG. 2B). The configuration of recessed cartridge storage receptacle 160 with spring 162, mounting features 164, and tab 166 are merely one example configuration, and any other techniques may be used to secure therapeutic fluid cartridges to device 100 when not in use. Or in other examples, cartridge storage receptacles 160 may be omitted and therapeutic fluid cartridges may be stored separately from device 100.

As shown in FIG. 2C, once therapeutic fluid cartridge 150A is removed from its cartridge storage receptacle 160, the user positions therapeutic fluid cartridge 150A within bay 170A for connection to port 172A. Similarly, empty cartridge 151 is positioned within bay 170B for connection to port 172B.

Locking mechanisms 180A, 180B (collectively, "locking mechanisms 180") are configured d to receive cartridges 150A, 151 for connection to ports 172A, 172B (collectively, "ports 172"). Each locking mechanism includes a plate 184 slidably mounted over pins 186. Plate 184 includes mounting features 182 to engage a mouth of a cartridge. In various example, mounting features 182 may include a press fit, screw threads, gasket and/or other connection features. Plate 184 is configured to engage brackets 188 with pointed tube 185 entering and fluidly engaging port 172A. For example, port 172A may include a seal that is punctured by pointed tube 185 as plate 184 is slid over pins 186 to engage brackets 188. Once plate 184 is slid over pins 186 to engage brackets 188, the cartridge 150A 151 is in fluid communication with the associated port 172. In this manner, therapeutic fluid cartridge 150A is engaged with therapeutic fluid cartridge port 172A, the therapeutic fluid cartridge 150A including a therapeutic fluid 120. Likewise, cartridge 151 is engaged with the cartridge port 172B, cartridge 151 providing unused volume available to store fluid from the fluid inlet 112.

Fluid outlet 128 is in fluid communication with the therapeutic fluid cartridge port 172A. Fluid pump 124 configured to deliver a therapeutic fluid 120 from a fluid cartridge 150 engaged with the therapeutic fluid cartridge port 172A through the fluid outlet 128 in response to fluid outlet control signals from control module 130. Similarly, fluid inlet 112 in fluid communication with the cartridge port 172B, and fluid control structure 114 in fluid communication with the fluid inlet 112 to control fluid flow through fluid inlet 112 and into cartridge 151. In various examples, fluid control structure 114 includes an inlet pump and/or an inlet valve.

Tubing segment 140 is in fluid communication with fluid outlet 128, fluid pump 124 and therapeutic fluid cartridge 150A by way of a direct connection to fluid outlet 128. In this manner, therapeutic fluid 120 is within the portion of fluid flow path 110 including fluid pump 124 and fluid outlet 128. With its connection to fluid outlet 128, tubing segment 140 delivers therapeutic fluid 120 from therapeutic fluid cartridge 150A to a joint capsule of a patient, such as right knee 40 (FIG. 1A), left elbow 22 (FIG. 1B) or other synovial joint of patient 10.

As also shown in FIG. 2D, device 100 further includes a fluid inlet 112, and a fluid control structure 114 in fluid communication with fluid inlet 112 and cartridge 151. Housing 101 contains the fluid pump 124, which is in fluid communication with fluid outlet 128, and fluid control structure 114, which is in fluid communication with fluid inlet 112. Fluid control structure 114 is configured to control fluid flow through fluid inlet 112 to fill cartridge 151 in response to control signals from a control module 130 as part of a flow path 110 through the joint capsule of the patient.

Tubing segment 142 is in fluid communication with fluid inlet 112, fluid control structure 114, and therapeutic fluid cartridge 150A by way of a direct connection to fluid inlet 112. Tubing segment 142 facilitates draining the joint capsule of the patient while tubing segment 140 delivers therapeutic fluid 120 to the joint capsule. Flow path 110 continues through tubing segment 142, enters the joint capsule of a patient before returning to device 100 via through tubing segment 142 and fluid inlet 112. While therapeutic fluid 120 may be diluted with synovial fluid of a joint capsule during treatment of a patient, the flow from tubing segment 142 means that therapeutic fluid 120 may be within the entirety of fluid flow path 110 including fluid outlet 128, tubing segment 140, a joint capsule of a patient, tubing segment 142, and fluid inlet 112.

Control module 130 sends control signals to fluid control structure 114 and fluid pump 124. Control module 130 is configured to receive cartridge identification data and output, based on the cartridge identification data, output fluid inlet control signals to operate the fluid control structure 114 and fluid outlet control signals to operate the fluid pump 124, according to a preprogrammed parameters associated with the cartridge identification data.

In some examples, control module 130 receives cartridge identification data from user interface 104. For example, a user may provide indication of a cartridge engaged with the therapeutic fluid cartridge port 172A to user interface 104. In turn, user interface 104 may output the cartridge identification data corresponding to the identified cartridge to the control module 130.

In the same or different examples, control module 130 receives cartridge identification data from a cartridge sensor 179. Cartridge sensor 179 configured to identify a cartridge engaged with the therapeutic fluid cartridge port 172A and further configured to output the cartridge identification data corresponding to the identified cartridge to the control module 130. For example, cartridges 150 each includes an ID label 159A-159D (collectively, "labels 159"), such as a barcode or other marking, memory, RFID or other technique storing cartridge identification data. In turn, sensor 179 detects cartridge identification data. In various examples, sensor 179 may include a wireless radio frequency (RF) sensor, an optical sensor, a mechanical sensor, a data port for connection to memory of ID label 159A and/or another sensor. In some examples, the mouth of cartridge 150 may vary in shape and thickness, and cartridge sensor 179 would be part of locking mechanisms 180A in order to sense the physical shape of the mouth to identify the cartridge 150.

In the same or different examples, therapy protocols may be stored with each cartridge 150 rather than preprogrammed as part of device 100. For example, ID label 159A may include memory include therapy protocols for delivery of the therapeutic fluid within cartridge 150A. The protocols are then read by cartridge sensor 179. In such examples, ID label 159A may encode digital information containing the therapy protocols.

In some examples, device 100 may redundancies in that such that the protocol of fluid circulation may be automatic initiation based on identification through cartridge sensor 179, but the automatic initiation may be overridden or manually entered by user interface 104, for example, based on the preferences of the user or if automatic initiation fails for any reason.

In the same or different examples, cartridges 150 could be color coded based on class of medication and numbered for compound within that class. For example, antibiotics could be green, green 1 could be vancomycin, 2 copra, etc. Such examples may simplify selection of the cartridge to mitigate user errors. In the same or different examples, user interface 104 may present an identification of the cartridge to a user based on detection by sensor 179, and require user confirmation before initiating a therapy protocol.

Device 100 further includes fluid sensor 126, which is located between fluid pump 124 and fluid outlet 128. Fluid sensor 126 is configured to monitor therapeutic fluid 120 between fluid pump 124 and fluid outlet 128 and further configured to output sensor data corresponding to a monitored condition of therapeutic fluid 120 to control module 130. Likewise, optional fluid sensor 115 may monitor a condition of therapeutic fluid 120 between fluid inlet 112 and fluid control structure 114, and transmit sensor data based on monitored condition of therapeutic fluid 120 control module 130. In various examples, the sensor data may include fluid pressure data and/or fluid flow rate data. Flow sensors may include optical sensors, pinwheel sensors, and others. Pressure sensors may be located outside flow path 110 and sense pressure through a membrane.

In the same or different examples, control module 130 may also determine fluid flow rates through fluid outlet 128 and fluid inlet 112 based on data communications with fluid control structure 114 and fluid pump 124. For example, fluid control structure 114 and/or fluid pump 124 may include a peristaltic pump or other pump such that the pump components do not come in direct contact with fluid flowing through the pump. In some examples, such as a peristaltic pump or piston pump, flow rates may be determined directly by the operation of fluid pump 124, such as directly from control signals sent to the peristaltic pump by control module 130. In the same or different examples, fluid control structure 114 and/or fluid pump 124 may including sensing capabilities, and may transmit operational data and/or sensor data, such as fluid pressure data and/or fluid flow rate data, to control module 130. In specific examples, such a peristaltic pump of fluid pump 124 may include a direct current motor operable in a range of 1-20 volts, such as a range of 5-6 volts.

Based on known characteristics of the fluid flow, including sensor data from fluid sensors 115, 126, control module 130 is configured to send control signals to operate fluid control structure 114 and fluid pump 124 to circulate therapeutic fluid 120 through a joint capsule 50 of a patient 10 according to preprogrammed flow rates while maintaining a positive fluid pressure within joint capsule 50 of patient 10. For example, control module 130 may operate fluid pump 124 to maintain preset flow rate(s) and may further operate fluid control structure 114 to maintain a desired pressure within a joint cartridge bay of a patient based on fluid pressure data from fluid sensor 126. In different examples, flow rates and/or pressures may be held constant or may be adjusted over time as desired to support the efficacy of therapeutic fluid 120.

Optional fluid filter 116 is positioned between fluid pump 124 and fluid sensor 126. The filter is located upstream of fluid sensor 126 such that any pressure drop through fluid filter does not impact the fluid characteristics sensed by fluid sensor 126. Fluid filter 116 may catch contaminants or other particulates during treatment thereby preventing reentry of injurious materials into the joint capsule. Other examples may include more or less filters at any point along flow path 110 within device. Other examples may not include filters.

Device 100 further includes a coating 111 along one or more components of flow path 110. As shown, coating 111 is on an interior surface of port 172A. Coating 111 is configured to inhibit protein and cell adhesion within fluid flow path 110. Coating 111 may be utilized some or all components of device 100 forming fluid flow path 110, such as fluid inlet 112, fluid control structure 114, fluid filter 116, Therapeutic fluid cartridge 150A, fluid pump 124, fluid sensor 126, and/or fluid outlet 128. Tubing segments 140, 142 and/or needles 141, 143 may also include coating 111.

Coating 111 may be configured to reduce protein aggregation on negatively charged, hydrophobic surfaces, and platelet adhesion to artificial surfaces, thereby activating both alternative and classical compliment pathways, releasing TxA2, ADP & WBC adhere to absorbed fibrinogen via CD IIb/CD18 w/ interaction between P-selectin on platelet surface and WBC P-selecten glycoprotein ligand 1, selected coatings may inhibit FXIIa upon hydrophilic surfaces. Such coatings may include one or more of: polyethylene oxide (PEO), pyrolytic carbon coating, elastin inspired polymer, aurintricarboxylic acid and/or a hydrophilic coating, such as a hydrophilic coating configured to inhibit thrombin PEG-CTI via FXIIa inhibition. In addition, or as an alternative to coating 111, the components of device 100 along flow path 110 may be formed form polymers configured to reduce platelet adhesion. Compounds such as, but not limited to these examples, will be employed so as to reduce said aggregation and thus improve efficacy and reduce pain experienced by patient.

In the same or different examples, coating 111 and/or filter 116 may include proteins along artificial surfaces mediate the attachment of platelets, leukocytes, and red blood cells to artificial surfaces. Further, proteins more often adsorb to hydrophobic surfaces than hydrophilic surfaces, independent of flow. Along metallic surfaces such as titanium, blood coagulates outside the vascular system independent of low protein adsorption to or activation by surfaces, due to the absence of an active down-regulation of procoagulative processes by the vascular endothelium. However, coating 111 and/or one or more of filters 116 may be configured to reduce this procoagulative process by including materials such as, polyethylene oxide (PEO), pyrolytic carbon, elastin inspired polymer, and aurintricarboxylic acid. In addition, selected elements along flow path 110, such as filter 116, may be negatively charged to attract procoagulative factors. Other elements along the flow path 110 may have a neutral or positive electrical charge to reduce this procoagulative process.

Device 100 includes a user interface 104, a battery 132, a charging port 134, and a data port 136 to support the operation of device 100 in the delivery of therapeutic fluid 120 to a joint capsule of a patient. Battery 132 is configured to supply electrical power to components of device 100, such as fluid pump 124, fluid control structure 114, and control module 130, whereas charging port 134 is operable to charge battery 132. In some examples, charging port 134 may also be used to directly power components of device 100. Other examples may not include a battery, in which case an external power source, such as an electrical plug may be used to power components of device 100.

User interface 104 facilitates presentation of information to a user of device 100, such as a clinician or patient 10, whereas data port 136 facilitates data transmissions with external devices. User interface 104 may facilitate programming therapy parameters, including such as, but not limited to cartridge identification information, and/or transmission of information related to device 100 operations over time or in real-time. In various examples, user interface 104 may include one or more of a visible display, audible alerts, keypads or other inputs, and or connection to a personal electronic device, such as wired or wireless connection to a user's cell phone.

Similarly, data port 136 may facilitate a wired and/or wireless connection to an external device. Example wired or wireless connections include USB, Wi-Fi, Bluetooth, cellular transmissions, as well as any other transmission standards suitable to support the operations of device 100. Data port 136 may facilitate programming therapy parameters, and/or transmission of information related to device 100 operations over time or in real-time. Data port 136 may also facilitate remote monitoring and/or programming of device 100 by a clinician. In some examples, such as USB, data port 136 may be combined with charging port 134 as a unitary component.

As shown in FIG. 3, joint capsule 50 encloses the knee 40 formed by femur 42, tibia 44, and fibula 46. The patella of knee 40 is not shown. Soft tissues of knee 40 illustrated in FIG. 3 include lateral meniscus 52, medial meniscus 53, lateral collateral ligament 54, medial collateral ligament 55, anterior cruciate ligament 56, and posterior cruciate ligament 58. Treatment of knee 40 by delivering therapeutic fluid 120 with device 100 may promote healing of any of these tissues. For example, completely torn ligaments, torn or worn meniscus, worn cartilage, and arthritis may benefit from treatment utilizing device 100. In some examples, treatments with device 100 may be combined with surgical intervention to repair tissues, either before or after surgery.

FIG. 3 further illustrates a needle 141 in fluid communication with tubing segment 140. Needle 141 accesses joint capsule 50 through skin 48 to facilitate infusing joint capsule 50 with therapeutic fluid 120 via fluid outlet 128 of portable joint capsule fluid delivery device 100 and tubing segment 140. In addition, needle 143 accesses joint capsule 50 through skin 48 to facilitate draining joint capsule 50 via tubing segment 142 and fluid inlet 112 of portable joint capsule fluid delivery device 100. Fluid flow path 110 includes tubing segment 140, needle 141, joint capsule 50, needle 143, and tubing segment 142. As discussed previously, fluid flow path 110 further includes circulating flow through joint capsule 50 before returning to portable joint capsule fluid delivery device 100. While not shown, needles 141, 143 may be secured with bandages or tape, and the entry points of needles 141, 143 through skin 48 of patient 10 may likewise be covered with bandages, wraps and/or antiseptics to maintain a sterile environment.

In both FIG. 1A and FIG. 1B, device 100 is secured to a limb of patient 10 with straps 102. Specifically, with respect to FIG. 1A, device 100 is secured to the front of thigh 32 of right leg 30, and with respect to FIG. 1B, device 100 is secured to the side of right left arm 20 above left elbow 22. These positions are merely examples and other positions may be selected by a clinician and their patient for comfort during treatment of patient 10 with device 100.

While device 100 is secured with straps 102, the treated joint remains mobile. In some cases, a clinician may immobilize the joint during treatment of the joint with device 100. In other examples, the clinician may prescribe movement of the joint during treatment of the joint with device 100, for example to support the removal of loose bodies with fluid flow created by device 100 through the joint capsule.

The portability of device 100 allows patient 10 to receive treatment of device 100 outside of a clinical setting. Therapies, including infusions, could be provided, in remote locations away from clinical settings, and during transport, such as when patients are moved across changing terrain. In addition, device 100 may continue therapies once a patient is moved to a clinical setting.

The mobility afforded patient 10 may also allow for long-term treatment with device 100, such as 4, 6, 8, or 12 hours per day, with a reduced impact on daily activity of patient 10. For example, a prescribed treatment of the joint of the patient may include operation of device 100 for a number of hours per day every day any number of days, such as 3 days, 7 days, or even weeks.

Cartridges 150 may provide any number of therapeutic fluids to be used in combination with device 100 according to the needs of patient 10. In various examples, therapeutic fluid 120 may include living cells to support natural regeneration of patient tissues with a joint capsule, such as, but not limited to stem cells, platelet-rich plasma (PRP), mesenchymal stem cells, and/or microfragmented adipose tissue (MFAT). In the same or different examples, therapeutic fluid 120 may include lubricants, such as Wharton's jelly. In the same or different examples, therapeutic fluid 120 may include fluids to support flushing a joint capsule, which may help remove loose bodies. Such flushing fluids may include saline, hypertonic saline, and/or hyperosmolar sugar solution. In the same or different examples, therapeutic fluid 120 may include components to sterilize and/or treat infections within a joint capsule, such as hydrogen peroxide, povidone-iodine, and/or antibiotics. In the same or different examples, therapeutic fluid 120 may include any number of pharmaceuticals to support treatment of the joint of a patient, including but not limited to, painkillers, steroids, antiseptics, and others.

Device 100 can be configured in advance so as to reduce time and contamination risk in any clinical setting where sterility is of concern such as angiography (that example follows). Further, the configuration also allows for delivery of therapies (i.e. antibiotics or thrombolytics) to soft tissues requiring tissue debridement such as abscesses, intra-muscular hematomas, intraparenchymal hemorrhages. Fluid collected could then be assayed and cultured to assess for resolution/cause of injury.

Cartridges 150 may come in pre-mixed and on-the-spot divisions. Pre-mixed would be for compounds either frequently used or needed for urgent use. Further, the pre-mixed tubing and containers will likely not have issues with adhesion of blood products. So in this category, iso-osmotic (normal saline, ringers) and hyper osmotic fluids to stimulate inflammation like hypertonic saline or glycosylated sugar solutions. Antibiotics, hydrogen peroxide, iodine, pain medications like morphine, fentanyl, sedative agents ketamine and propofol (0.5 mg/Kg 50/50 both), anticonvulsants valium and Ativan, nerve agents atropine and pralidoxime chloride.

In the on-the-spot division, will typically be compounds for rehabilitation and recovery from the patient themself. This would include PRP, microfragmented adipose tissue, stem cells. Wharton's Jelly too. These compounds could all circulate for tissue recovery, irrigation, and debridement.

Another potential use could be to aid in angiography. Assembling an array of tubes, 10-15 mL of iodinated contrast pre-packaged and sterile could improve angiography work flow by reducing time to fill these tubes in a procedure and ensure no air bubbles in the assembly.

As these examples illustrate, device 100 may be combined with any number of available therapeutic fluids to support the treatment of a joint capsule. The portability of device 100 allows such treatments to occur for longer periods of time than procedures occurring within a clinical setting, such as injections or flushing. Extending period of time therapeutic fluids are delivered to a joint capsule may improve the efficacy of the therapeutic fluids by other means.

Figure 4:
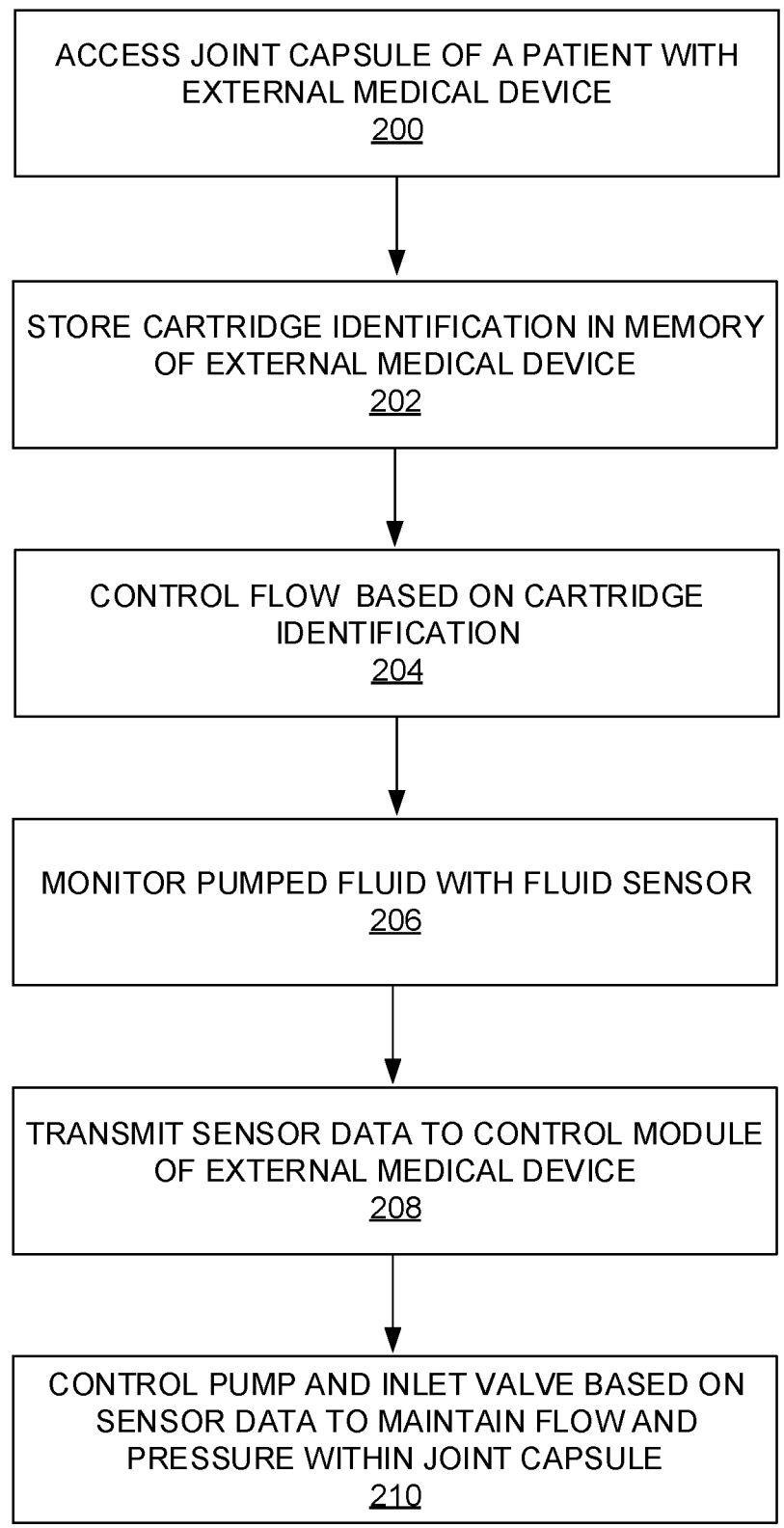
FIG. 4 is a flowchart illustrating a method for delivering fluid to a joint capsule of a patient.

FIG. 4 is a flowchart illustrating a method 200 for delivering fluid to a joint capsule of a patient. For clarity, the techniques of FIG. 4 are described with respect to portable joint capsule fluid delivery device 100 and right knee 40 of patient 10, although the techniques may likewise be applied to other joints, such as left elbow 22 of patient 10, and to variations of the joint capsule fluid delivery devices disclosed herein.

First, a user, such as a clinician or a patient, accesses a joint capsule of a patient to fluidly connect fluid inlet 112 and fluid outlet 128 of device 100 (200). For example, a clinician may first disinfect skin 48 using a common disinfectant, such as a solution including alcohol, iodine and/or chloraprep. Next, the clinician may insert needles 141, 143 to access joint capsule 50. For example, examples, needles 141, 143 may be relatively large, such as 14 gauge, (1.6 millimeters (mm) internal diameter) to facilitate therapy, such as flushing and removal of loose bodies from within joint capsule 50. In some examples, the clinician may utilize an imaging system, such as ultrasound, to assist in the proper placement of needles 141, 143. In some further examples, a catheter or stent, such as an expandable stent, may be used to increase the diameter of the access into joint capsule 50 beyond that provided by needles 141, 143, such as to a diameter of at least 4 mm, such as to a range of 6 mm to 8 mm. In such examples, the stent or catheter may remain in place during the delivery of therapeutic fluid 120 by device 100 in lieu of needles 141, 143 within the flow path 110 to maintain a larger access to joint capsule 50.

Following the access to joint capsule 50 with needles 141, 143 and/or a larger stent or catheter, device 100 is operated to begin therapy. Device operation is based on storing an identification of a therapeutic fluid cartridge 150A in a memory of a control module 130 (202). In some examples, the method includes receiving, with the control module 130, the identification of the therapeutic fluid cartridge 150A from a cartridge sensor of the external medical device. In the same or different examples, the method further includes receiving, with the control module 130, the identification of the therapeutic fluid cartridge 150A from user interface 104. In addition, cartridges may be color-coded or include other markings to aid in identification by a user.

In particular, control module 130 actives fluid pump 124 to pump therapeutic fluid 120 from therapeutic fluid cartridge 150A into joint capsule 50 of patient 10 via fluid outlet 128 and tubing segment 140 according to control signals from control module 130 based on the stored identification. The method also includes sending instructions based on the stored identification, from the control module 130 to a fluid control structure 114 of the external medical device, to operate the fluid control structure 114 in order to control flow from the joint capsule 50 via a tubing segment 142 into a cartridge 151 via a fluid inlet 112 of the external medical device (204). In addition, a user may override a control program associated with a cartridge through the user interface 104, either by selecting a different program or by manual selection of one or more therapy parameters. Such a feature may be particularly useful in an emergency situation, for example, to deliver a therapeutic fluid more quickly than provided for by the preset therapy program associated with a particular therapeutic fluid cartridge.

Filter 116 filters fluid flowing through fluid outlet 128. Tubing segments 140, 142 and stents or catheters in lieu of needles 141, 143 may provide a relatively large diameter, such as 1 centimeter or more, such as 1.6 centimeters in order to facilitate a desired flow rate with a limited pressure drop through tubing segments 140, 142. For example, a flow rate may be at least 1 milliliter per second, such as within a range of 2-3 milliliters per second.

Fluid inlet 112 is in fluid communication with cartridge 151 such that flow through fluid inlet 112 fills cartridge 151. The fluid flowing through fluid inlet 112 may include therapeutic fluid 120 which has passed through joint capsule 50, although the original concentration of therapeutic elements within therapeutic fluid 120 may be diluted with bodily fluids, such as synovial fluid.

Also, during the delivery of therapeutic fluid 120 to joint capsule 50, fluid sensor 126 monitors a condition of therapeutic fluid 120 between fluid pump 124 and fluid outlet 128 (206). Fluid sensor 126 further transmits sensor data based on monitored condition of therapeutic fluid 120 control module 130 (208). Likewise, optional fluid sensor 115 may monitor a condition of therapeutic fluid 120 between fluid inlet 112 and fluid control structure 114, and transmit sensor data based on monitored condition of therapeutic fluid 120 control module 130.

Based on the sensor data from fluid sensor 126, and the cartridge identification information, control module 130 sends fluid inlet control signals to fluid control structure 114 and fluid outlet control signals to fluid pump 124 to circulate therapeutic fluid 120 through joint capsule 50 of patient 10. The control signals may correspond to preprogrammed flow rates while maintaining a positive fluid pressure within joint capsule 50 of patient 10 based on the cartridge identification (210). For example, control module 130 may restrict flow through fluid control structure 114 to maintain a pressure of 20-80 mm of mercury (mmHg), such as pressure of about 40 mmHg.

Device 100 may be programed to provide any number of flow rates and pressures over time. In one example, device 100 may operate fluid pump 124 to circulate therapeutic fluid 120 through joint capsule 50 continuously or near continuously over a period of time, such as 4-12 hours, such as 8 hours. Fluid pumped into joint capsule 50 through tube segment 140 may drain through tube segment 142 at approximately the same flow rate as fluid is pumped into joint capsule 50. In some examples, fluid control structure 114 may be operated to maintain a positive pressure within joint capsule 50, or to cycle between a positive pressure and unrestricted flow. In other examples, fluid control structure 114 may be completely open in order to not restrict flow. In yet further examples, fluid control structure 114 may include a pump, such as a peristaltic pump, to create a negative pressure and draw fluids through tube segment 142.

In other examples, device 100 may operate fluid pump 124 to inflate joint capsule 50 with therapeutic fluid 120. Once operation of fluid pump 124 creates a desired pressure and/or volume fluid pump 124 may cease pumping. After a set period of time, such as 1 hour, fluid control structure 114 may open to drain excess fluid from joint capsule 50.

In any configuration of fluid control structure 114, programming may optionally include a stages of draining fluid from the joint capsule 50 prior to, coincident with and/or after pumping fluid from a cartridge 150 into the joint capsule. For example, draining excess fluid from the joint capsule before pumping fluid from a cartridge 150 into the joint capsule may increase the concentration of the therapeutic fluid within the joint capsule, potentially improving the efficacy of the therapeutic fluid. Fluid control structure 114 may drain or suck out infection in combination with, or separate from, delivery of fluids by fluid pump 124.

Device 100 may also be used in applications outside of delivering, draining and circulating fluid from a joint capsule of a patient. For example, device 100 may not only access capsular joints, but also to provide serial injections are needed, such as angiograms, and other medical applications, such as irrigating abscesses or infusion of medications anywhere within the body of patient, such as muscular tissues, skeletal tissues, vascular system or nervous system. In some examples, therapy may include delivery of fluid by fluid pump 124, but not draining of fluid with fluid control structure 114. In other examples, fluid control structure 114 may drain or pump of a fluid from a patient separate from the delivery of fluid by fluid pump 124. For example, device 100 may provide infusion of any intravenous medications requiring a pump. Thus, device 100 is suitable to support a multitude of medical therapies and treatments including delivery and/or removal of fluid.

The specific techniques for delivering and removing fluids from a patient, such described with respect to portable joint capsule fluid delivery device 100, are merely illustrative of the general inventive concepts included in this disclosure as defined by the following claims.

The invention claimed is:

1. An external medical device comprising:
 a housing;
 a first cartridge bay with a first cartridge port, wherein the first cartridge bay is formed from a first recess within the housing, the first recess sized to contain a first cartridge engaged with the first cartridge port within an outer profile of the housing;
 a second cartridge bay with a second cartridge port, wherein the second cartridge bay is formed from a second recess within the housing, the second recess sized to contain a second cartridge engaged with the second cartridge port within the outer profile of the housing;
 a fluid outlet in fluid communication with the first cartridge port;
 a fluid pump configured to deliver a therapeutic fluid from a fluid cartridge engaged with the first cartridge port through the fluid outlet in response to fluid outlet control signals;
 a fluid inlet in fluid communication with the second cartridge port; and
 a fluid control structure in fluid communication with the fluid inlet to control fluid flow through the fluid inlet.

2. The external medical device of claim 1, further comprising:
 the first cartridge engaged with the first cartridge port and contained within the first recess, the first cartridge including the therapeutic fluid; and
 the second cartridge engaged with the second cartridge port and contained within the second recess, the second cartridge providing unused volume available to store fluid from the fluid inlet.

3. The external medical device of claim 1, further comprising a control module configured to output fluid inlet control signals to operate the fluid control structure and the fluid outlet control signals to operate the fluid pump.

4. The external medical device of claim 3, wherein the control module is configured to receive cartridge identification data and output, based on the cartridge identification data, the fluid inlet control signals to operate the fluid control structure and the fluid outlet control signals to operate the fluid pump, according to preprogrammed parameters associated with the cartridge identification data.

5. The external medical device of claim 4, further comprising a cartridge sensor configured to identify a cartridge engaged with the first cartridge port and further configured to output the cartridge identification data corresponding to the identified cartridge to the control module.

6. The external medical device of claim 5, wherein the cartridge sensor includes one or more of a group consisting of:
 a wireless radio frequency (RF) sensor;
 an optical sensor; and
 a mechanical sensor.

7. The external medical device of claim 4, further comprising a user interface configured to receive an indication of a cartridge engaged with the first cartridge port from a user, and further configured to output the cartridge identification data corresponding to the indication of the cartridge to the control module.

8. The external medical device of claim 3, further comprising a fluid sensor configured to monitor the therapeutic fluid between the fluid pump and the fluid outlet and further configured to output sensor data corresponding to a monitored condition of the therapeutic fluid,
 wherein the control module is configured to receive the sensor data and output, based on the sensor data, the fluid inlet control signals to operate the fluid control structure and the fluid outlet control signals to operate the fluid pump.

9. The external medical device of claim 8, wherein the sensor data includes one or more of a group consisting of:
 fluid pressure data; and
 fluid flow rate data.

10. The external medical device of claim 1, wherein the housing contains the fluid pump and the fluid control structure, wherein the housing further forms a plurality of recessed cartridge storage receptacles.

11. The external medical device of claim 1, further comprising the therapeutic fluid within a fluid flow path including the fluid pump and the fluid outlet.

12. The external medical device of claim 11, wherein the therapeutic fluid includes one or more of a group consisting of:
 platelet-rich plasma (PRP);
 mesenchymal stem cells;

microfragmented adipose tissue (MFAT);
Wharton's jelly;
saline;
hypertonic saline;
hyperosmolar sugar solution;
hydrogen peroxide;
povidone-iodine; and
antibiotics.

13. The external medical device of claim 1, further comprising a coating configured to inhibit protein and cell adhesion within a fluid flow path including the fluid pump and the fluid outlet.

14. The external medical device of claim 1, wherein the fluid control structure includes at least one of a group consisting of:
an inlet pump; and
an inlet valve.

15. The external medical device of claim 1, further comprising a battery configured to supply electrical power to the fluid pump and the fluid control structure.

16. The external medical device of claim 1, further comprising a fluid filter within a flow path between the first cartridge port and the fluid outlet.

17. The external medical device of claim 1, further comprising:
a first tubing segment in fluid communication with the fluid outlet;
a first needle in fluid communication with the first tubing segment, the first needle being configured to access a joint capsule of a patient to facilitate infusing the joint capsule with the therapeutic fluid via the fluid outlet and the first tubing segment;
a second tubing segment in fluid communication with the fluid inlet; and
a second needle in fluid communication with the second tubing segment, the second needle being configured to access the joint capsule of the patient to facilitate draining the joint capsule via the second tubing segment and the fluid inlet.

18. A method for delivering a therapeutic fluid to a joint capsule of a patient, the method comprising:
storing an identification of a first cartridge in a memory of a control module;
sending instructions based on the stored identification, from the control module to a fluid pump of an external medical device, to activate the fluid pump in order to deliver the therapeutic fluid from the first cartridge via a fluid outlet of the external medical device into the joint capsule via a first tubing segment; and
sending instructions based on the stored identification, from the control module to a fluid control structure of the external medical device, to operate the fluid control structure in order to control flow from the joint capsule via a second tubing segment into a second cartridge via a fluid inlet of the external medical device,
wherein the external medical device includes:
a housing;
a first cartridge bay with a first cartridge port, wherein the first cartridge bay is formed from a first recess within the housing, the first recess sized to contain the first cartridge engaged with the first cartridge port within an outer profile of the housing;
a second cartridge bay with a second cartridge port, wherein the second cartridge bay is formed from a second recess within the housing, the second recess sized to contain the second cartridge engaged with the second cartridge port within the outer profile of the housing;
the fluid outlet, which is in fluid communication with the first cartridge port;
the fluid pump, which is configured to deliver the therapeutic fluid from the first fluid cartridge engaged with the first cartridge port through the fluid outlet in response to fluid outlet control signals;
the fluid inlet, which is in fluid communication with the second cartridge port; and
the fluid control structure, which is in fluid communication with the fluid inlet to control fluid flow through the fluid inlet.

19. The method of claim 18, further comprising receiving, with the control module, the identification of the first cartridge from a cartridge sensor of the external medical device.

20. The method of claim 18, further comprising receiving, with the control module, the identification of the first cartridge from a user interface of the external medical device.

* * * * *